Oct. 21, 1969 S. CALVINO Plant Pat. 2,932
ROSE PLANT
Filed Sept. 22, 1967
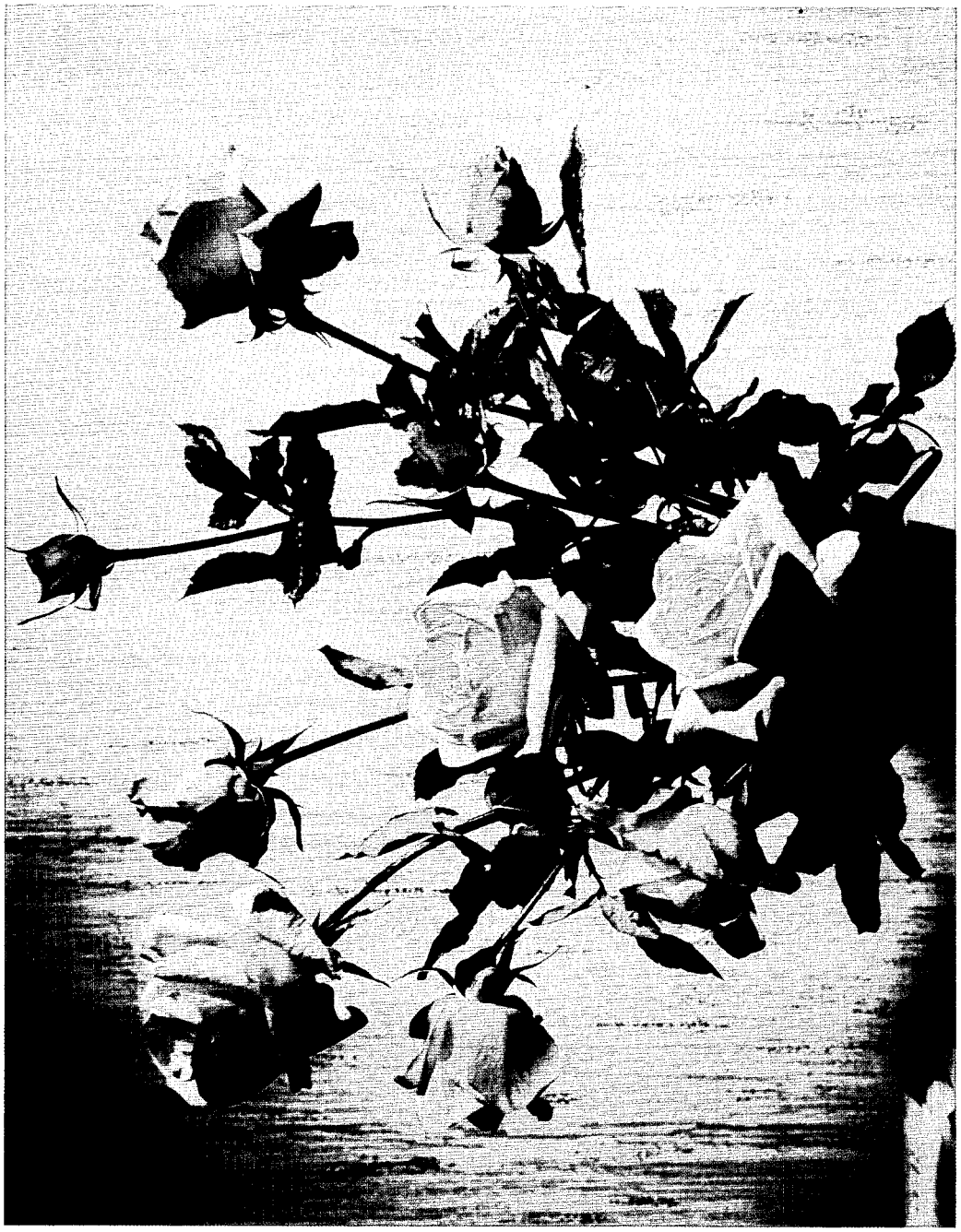

United States Patent Office

Plant Pat. 2,932

Patented Oct. 21, 1969

2,932

ROSE PLANT

Stefano Calvino, Strada Coldirodi 65, Sanremo, Italy

Filed Sept. 22, 1967, Ser. No. 669,981
Claims priority, application Italy, Nov. 30, 1966, 43,216/66
Int. Cl. A01h 5/02
U.S. Cl. Plt.—19 1 Claim The aim of this present invention was to obtain a new variety of rose, better than the varieties commonly grown, and more suitable for supplying the most recent needs of international flower markets. A rose of a bright pink, tending to red, has been lacking on the market for some time, and thus the applicant suggested carrying out research to find this particular variety, using various opportune methods.

The plant required had to have not only the tonality of color desired, but also all the other characteristics which qualify the commercial rose; in other words, a graceful flower shape, easily opening corolla, petals of good consistency, resistant to packing and transport, resistance of flower color to atmospheric difficulties; vigorous and strong growth, with stems and leaves in proportion to the flower, resistant to inclement weather and disease, simple to cultivate, and very productive in industrial cultivation.

The plant which is the subject of the present invention adheres in the greatest possible degree to the requirements which were the basis of the applicant's research, and can thus be considered as a positive result of the studies carried out.

The variety which is the subject of the present invention has been obtained by the genetic cross-breeding of different varieties of roses, appropriately chosen, according to the laws of genetic science.

After numerous fruitless attempts because of the difficulty of determining the variety to use in cross-breeding, it was at last possible to isolate, from a wide stock of hybrid varieties produced previously by the applicant with pollen of the type known commercially by the name of "Ninfa Rossa" the plant which is the object of the present invention, in which, with successive careful multiplication, it has been possible to fix the necessary requisites. The variety "Ninfa Rossa" is here identified as a sport (lusus naturae) of the variety Nymph obtained by A. Dickson in 1953 and which was derived from the variety Fashion × unnamed seedling, which has varied the color coral-salmon of its flowers. Nymph variety is named in "Modern Roses V" Ed. McFarland New York, page 279, and in "American Rose Annual" 1966—Ed. American Rose Society, page 229.

The variety which is the subject of the present invention need not be reproduced by repeating the cross-breeding carried out in order to obtain it. Such operations constitute a laboratory procedure which is not necessary in order to produce the invention. It can in fact be easily reproduced and multiplied in any number of specimens and thus on an industrial scale, on the part of the breeder, by means of one of the vegetative reproduction methods commonly used in floriculture (cutting, grafting, layering, etc.) and in particular by grafting axillary buds of the plant according to the present invention or of another plant derived from it by vegetative means, on graft recipients suitable for the soil on which it is intended to carry out the cultivation.

When repeatedly reproduced by this method, the plant which is the subject of the present invention has constantly and faithfully transmitted all its distinctive characteristics in its subsequent descendants, making its cultivation possible for the production of cut flowers for the market and for ornamental plants in parks and gardens.

The characteristics in their unique combination, which differentiate the variety which is the subject of the present invention from other varieties of its class, and which define it, follow in a list, provided as a non-limiting example in description, taken from a set of plants cultivated according to industrial criteria, in the open air and under glass, on a sunny hillside in the month of October.

It is always necessary to bear in mind the season and the climate in order to evaluate any possible difference in characteristics that may occur due to diverse conditions. These differences must be considered normal at least until, repeating the cultivation of the plant described, in the same conditions, it is possible to identify the plant by means of the collection of the characteristics given in the description.

The naming of the colors in the description have been made according to the tables of the "Horticultural Color Chart" by Robert F. Wilson (indicated in the text by the initials HCC), except in the cases where the color was absent from the tables or where its indication was sufficiently clear according to common parlance.

Classification: Botanical and commercial—Hybrid tea rose

Stock: Unknown hybrid of HT with red flowers—"Ninfa Rossa." More particularly, the parentage is an unnamed HT seedling, red flowered × Ninfa Rossa. Pollen of the varietw Ninfa Rossa was used to fecundate the HT variety unnamed, this one being the mother plant.

PLANT

Growth: Very vigorous plant, large, bushy, erect vertical growth, with rather sparse leafage, of rapid growth.

Average height: For plants completely developed, grafted about two years previously on *Rosa indica major,* cultivated in greenhouses, 180–220 cm.

Roots: Shapes and sizes varying according to the types of graft recipient used in the multiplication. In the plants described, the roots were sturdy, not very numerous, embedded in soil, little ramification, with scarce root hairs, average length 40–60 cm. and average diameter at collar of 4–12 mm.

Stem: Varying in shape and dimensions according to the type of graft recipient. In the plants described, it was constituted by the cutting of a *Rosa indica major* used in the grafting, cylindrical, average length 25–30 cm. and the diameter at the collar of 10–15 mm.

Main branches: Average number 2–6, starting from the grafting point or from the other main branches at intervals of length 40–60 mm.

*Shape.*—Approximately cylindrical, conical, thinning towards the top, articulated in numerous internodes of average length 40–60 mm. with small nodes, averagely differentiated, swollen when carrying secondary branches.

*Sizes.*—Varying according to the method of pruning used in the forming of the plant. Average length 40–60 mm. or more. Average diameter at base 7–15 mm.

*Bark.*—Thick, smooth or slightly lined lengthwise.

*Color.*—Close to sage green (HCC, page 198, shades 61/1–2–3) with tonality of spinach green (HCC, page 187 shades 60/2–3) in the new shoots of the year.

*Consistency.*—Woody, firm.

*Thorns.*—Averagely thick, sparse, of medium size, almost isodimensional, mingled with smaller thorns, easily detachable from the bark.

*Shape.*—Triangular with concave sides, long sharp point, straight or slightly inclined towards the base. Average length, 8–12 mm. Average breadth, 8–10 mm. Average thickness, 2–4 mm. Small thorns: length, 4–6 mm.; breadth, 3–5 mm.; thickness, 1–2 mm.

*Color.*—Dark nutbrown.

Flower stems: Average 2–6 for each main branch, generally inserted on the highest nodes of these, erect, firm, rising upwards, graceful.

*Shape.*—Cylindrical-conical, diameter slightly decreasing at the base of the apex, slender and elongated, articulated in numerous internodes of average length 50–90 mm. Nodes slightly differentiated, not rising up the stems.

*Average sizes.*—Length, 70–120 cm. Diameter at the base, 6–10 mm.

*Consistency.*—Woody or sub-woody, firm, resistant.

*Bark.*—Of medium thickness, smooth, hairless, opaque or slightly satiny, often pruinose and waxy.

*Thorns.*—Averagely numerous, thicker at the base of the stems, sparse, about 2–5 for every internode, easily detachable from the bark.

*Shape.*—Triangular, almost regular, with lower side more concave than upper, sharp point, averagely differentiated, straight or slightly inclined downwards.

*Size.*—Average length, 8–10 mm. Average breadth, 8–10 mm. Average thickness, 2–4 mm.

*Color.*—From one near to Egyptian buffalo (HCC, page 122 shades 7/1–2) tinged with nutbrown at the point, to one near pomegranate red (HCC, page 192, shades 18/3).

*Consistency.*—Averagely tender, resistant.

Leaves: Abundant, inserted singly on all the nodes, clothing the plant and the stems along their complete height in a harmonious and elegant way. The dark green of the leaves harmonizes well with the color of the flowers.

*Shape.*—Elongated and graceful, composed of from 3–5–7 folioles, more often 5–7, inserted in opposite pairs plus a terminal foliole, on a slender midrib.

*Size.*—Varying with the position on the plant, generally growing from the bottom towards the top. From average to large. Average length, from the base of the midrib to the apex of the terminal foliole, 120–160 mm. Average breadth between the extreme points of the opposite folioles, 70–100 mm.

*Arrangement.*—Little or averagely divergent from the stem to almost horizontal.

*Folioles.*—From average to large, elongated ovals, slightly spear-shaped, with an almost semicircular base and averagely sharp point, averagely differentiated. Limb flat or not very concave, V-shaped along the central nervations. Folioles almost flat on the foliar plan. Edges of the folioles finely saw-edged with teeth of average size.

*Size.*—Growing from the base of the leaf to the terminal foliole according to the following movement. First pair from the base: length, 28–35 mm.; breadth, 14–20 mm. Second pair from the base: length, 35–50 mm.; breadth, 25–35 mm. Third pair from the base: length, 45–55 mm.; breadth, 30–40 mm. Terminal foliole: length, 50–60 mm.; breadth, 40–50 mm.

*Color.*—Right side—between parsley green (HCC, page 193, shades 62/62/1) and leek green (HCC, page 197, shades 58/1–2). Underside—near to willow green (HCC, page 195, shades 62/62/1).

*Surface.*—Right side—smooth, hairless, a little satiny or averagely glossy. Veins pennate and marked reticulations on the limb. Underside—hairless, or not very glandulous, opaque or not very satiny.

Pennate nervation and raised reticulations on the limb.

*Consistency.*—Thin, leathery, resistant.

*Midrib.*—Thin, straight or not very curved, elongated, with longitudinal furrow on the right side, furnished with glandular hairs on the edges. Small thorns, 2–3 in number, lengths 3–4 mm.; very slightly hooked downwards on the underside of the midrib.

*Stipules.*—From medium to large, adnate at the edges of the first basic internode of the midrib, on about half its length, with hairy borders, slightly serrated; average auricles, diverging from the midrib at angles of 40°–50°. Average length, 2–4 mm.

FLOWER

Arrangement: Flowering at the top, with main flower terminal erect on the stem, surrounded by 1–5 secondary smaller flower buds, borne by strong lateral shoots inserted in the highest nodes of the stem. The main flower has a long slender peduncle, erect, firm, furnished with numerous needle-shaped thorns, length 1–2 mm., very thin and delicate.

Closed flower bud: Conical, with flat base and averagely pointed tip, surrounded by serrated foliaceous appendices and often hairy dentellations, which frequently disappear when the flowers are completely open. Small foliaceous appendices, of 8–10 mm. length and 1–2 mm. breadth are inserted on the sides of the sepals and diverging from the side of the bud.

*Average sizes.*—Length, 30–40 mm. Average diameter, 18–25 mm.

Semi-open flower bud: From averagely elongated oval to globose, with outer petals opening gradually with slight furling of the lateral borders.

*Average sizes.*—Length, 30–40 mm. Diameter 30–45 mm.

*Color.*—Between cherry red (HCC, page 157, shades 22–22/1) and rose red (HCC, page 158, shades 24–24/1–2) on the outside of the petals. Rose red (HCC, page 158, shades 24/2–3) on the inside of the petals and on the furling of the edges.

Open corolla: Calyx—composed of five sepals which open early in star shape and then fall back on the thalamus and on the floral peduncle.

*Thalamus.*—Differentiated, cup-shaped, almost hemispherical or slightly conical, a little tapering where the sepals are attached, average length 8–12 mm. and average diameter 8–10 mm.

*Sepals.*—Triangular, averagely elongated, slightly spear-shaped, terminate sometimes in a spear-shaped foliaceous appendix, but more often in a thin elongated tip, differentiated. Small spear-shaped appendices of length 8–10 mm. and breadth 1–2 mm. are inserted on an average number of 1–2 on the sides of the sepals and diverging from these at angles of 40°–50°. Sepal edges a little scaly. Limb of the sepal a little concave lengthwise.

*Size.*—Average length, 30–35 mm. Breadth at the base, 8–10 mm.

*Color.*—Near to lavender green (HCC, page 116, shades 61–61/1–2) covered with fine short woolly tomentum, at times washed with pomegranate red (HCC, page 192, shades 18/1–2) and Scheele green (HCC, page 175, shades 60–60/1) marked and streaked more or less widely with pomegranate red (HCC, page 192, shades 18/1–2).

*Surface.*—Right side—slightly tomentose; underside—smooth, hairless or a little glandular.

*Consistency.*—Thick, firm, leathery.

*Corolla.*—From medium to large, shape of hemispherical cup, with whorls of outside petals curving downwards. Center of flower concave, becoming raised, almost conical. Rounded festooned border or starred, with sharp tips formed by the borders of the outside petals. Central petals rather irregular and sometimes arranged dial-wise. Flat petals, furled on the lateral borders in outer whorls, curving outwards in the concave intermediate petals, towards the center of the flower in the central petals.

*Average sizes.*—Average diameter, on full opening, 80–100 mm. Length of flower from thalamus to the apex of the petals, 35–45 mm.

*General color.*—Near to ruby red (HCC, page 184, shades 22–22/1) with shades of cherry red (HCC, page 157, shades 22/2–3) in the parts in shade.

*Petals.*—Average number 40–50, inserted regularly on the thalamus.

*Shape.*—Outside petals—rounded limb, with lateral borders widely convergent on the claw, concave at the base, furled on the outside of the distal edge and on the lateral borders. Inside petals—oval limb, averagely elongated, furled at short intervals on the lateral borders, forming medium sharp tips at the meeting of the furls. Petaloid stamens of average number at the center of the flower.

*Sizes.*—Outside petals: average length, 45–55 mm.; average breadth, 25–35 mm. Inside petals: average length, 30–40 mm.; average breadth, 25–35 mm.

*Color.*—Right side, interior, rose red (HCC, page 184, shades 24/2–3) at the center of the limb, washed with oriental red (HCC, page 165, shades 19–19/1) in the lower third. Claw markings of Indian yellow (HCC, page 6, shades 6–6/1). Underside, exterior—rose red (HCC, page 158, shades 24/1–2) washed with cherry red (HCC, page 157, shades 22/22/1) in the lower part of the limb. Claw markings of Indian yellow (HCC, page 6, shades 6.2–3) smaller than on the outside petals.

*Surface.*—Right side—smooth, hairless, satiny, with reticulated veins grooved in limb. Underside—smooth, hairless, satiny, with slightly raised reticulated veins on limb.

*Consistency.*—Thick, fleshy, very resistant.

Organs of reproduction: Stamens—average 70–76 in number on the edge of the thalamus. Erect filaments of medium thickness, length, 9–12 mm. straight or slightly curved towards the inside of the flower, yellow in color. Anthers—large, bilocular oval, yellow. Styles—70–80, very fine, close at the base, freer at the distal extremity, greenish-white, often washed with pomegranate red. Stigmas of elongated cone shape at the apex of the styles, often washed with purple.

Fruit: Almost completely enclosed in the thalamus.

Perfume: Delicate, sweet tone of tea rose.

Resistance of flowers to inclement weather: Good.

Resistance of flowers to transport: Excellent.

Durability of cut flowers: Remarkable.

Resistance of plant to disease: The variety is very resistant to mildew, Oidium and black spot.

Resistance of plant to inclement weather: Excellent.

Flowering: Remarkable.

Simplicity of cultivation: Remarkable.

I claim:

1. Hybrid tea rose plant, whose first plant of this variety was obtained by artificial fecundation of the flowers of an unknown hybrid variety with pollen from the red flowers of the variety known as "Ninfa Rossa," characterized by the following unique combination of morphological and physiological features: sturdy, bushy and graceful plant, with medium-sparse vegetation, and medium branches diverging from the axis of the plant: numerous flower stems, erect and graceful, with foliage from medium to large in size, abundant, of a dark green color, averagely glossy; vigorous plant of rapid growth, highly re-flowering in industrial cultivation for the production of cut flowers, in all seasons, average occurrence of thorns, resistant to disease, mildew, Oidium and black spot; flowers from medium to large size, hemispherical in shape, slightly more elongated in the half-open bud, of a color near to ruby red with shades of cherry red, easily opening, resistant to inclement weather and to discoloration by the sun, of long duration once cut, resistant to packing and transport, lightly perfumed.

No references cited.

ROBERT E. BAGWILL, Primary Examiner